(12) United States Patent
Dado

(10) Patent No.: US 6,482,442 B1
(45) Date of Patent: Nov. 19, 2002

(54) SUBSTANCE MIXTURE FOR TOPICAL APPLICATION COMPRISING OLIVE OIL AND HONEY

(76) Inventor: Suleiman Dado, Landstrasse Haupstrasse 2, In der Hilton-Passage, A-1030 Vienna (AT)

( * ) Notice: Subject to any disclaimer, the term of this patent is extended or adjusted under 35 U.S.C. 154(b) by 0 days.

(21) Appl. No.: 09/696,346

(22) Filed: Oct. 24, 2000

Related U.S. Application Data

(63) Continuation of application No. PCT/AT99/00098, filed on Apr. 22, 1999.

(30) Foreign Application Priority Data

Apr. 24, 1998 (AT) .............................................. A 690/98

(51) Int. Cl.$^7$ ........................ A61K 35/64; A61K 35/37; A61K 35/78
(52) U.S. Cl. ........................ 424/539; 424/537; 424/725; 424/744; 424/746
(58) Field of Search .............................. 424/725, 195.1, 424/537, 539, 744, 746

(56) References Cited

U.S. PATENT DOCUMENTS 4,761,285 A  *  8/1988  Vasiliou et al.

FOREIGN PATENT DOCUMENTS

| GB | 2228411 | 8/1990 |
| RU | 2121341 C  * | 3/1996 |
| RU | 2100026 | 12/1997 |

OTHER PUBLICATIONS

Gruenwald, J. et al (eds.). PDR for Herbal Medicines. 1998. Medical Economics Company, Montvale, N.J., pp. 1113–1115.*

* cited by examiner

Primary Examiner—Christopher R. Tate
Assistant Examiner—Kailash C. Srivastava
(74) Attorney, Agent, or Firm—Fulbright & Jaworski L.L.P.

(57) ABSTRACT

The use of a substance mixture comprising honey and olive oil for preparing a medicament for topical application is suggested.

11 Claims, No Drawings

SUBSTANCE MIXTURE FOR TOPICAL APPLICATION COMPRISING OLIVE OIL AND HONEY

This application is a continuation of PCT Application No. PCT/AT99/00098 filed Apr. 22, 1999, which claims priority to Austrian Application No. A 690/98 filed Apr. 24, 1998.

The invention relates to the topical use of a substance mixture comprising honey and olive oil.

"Topical" here means the local, external treatment of skin parts. By applying a substance or a substance mixture onto the area to be treated, the ingredients can directly penetrate at the diseased location and act there. The alleviating and healing properties thus can become active immediately and precisely localized.

Agents presently in use for the treatment of hemorrhoids (node-shaped enlargement of the branches of the arteria or vena rectalis sup. in the region of the corpora cavernosa recti supplied with arterial or venous blood) very often contain corticoids whose use, however, on account of the severe side effects, involves great difficulties and risks. At present, there also exist some corticoid-free medicaments, such as Acetonal-Hämorrhoidal®, Hädensa®, Mucotherm-Z äpfchen® (suppositories), Sperti Präparation® or Sulgan®, to mention but a few, wherein a hypersensitivity to one of the components of these preparations may occur with any one of them. With the two last mentioned medicaments, however, also allergic reactions may occur. Furthermore, these agents do not lead to a quick and certain healing, but in most cases have an alleviating effect only.

The loss of hair may have various causes, it may, e.g., be caused by old age, or it may be a consequence of radiation or chemotherapy in tumour treatment. Dandruff may be caused by external influences or by internal or infectious diseases. A number of agents have been described for hair and scalp care, such as, e.g., capsules to be swallowed, electrical pulses for activating cell functions, hair lotions, shampoos or hair packs. These treatments have to be carried out over longer periods of time and often have side effects or lead to counter-reactions or remain unsuccessful, respectively.

Skin problems may have the most varying causes, such as damaging environmental influences (sun, air pollution), allergies, hormonal imbalance, bad eating habits, the taking of medicaments (antibiotics), wounds etc., and they occur more and more frequently. Many creams are aggressive, damage the sensitive skin parts and dehydrate them.

Varicose veins (primary or secondary varicosis) form on account of a mechanical impediment in the venous flow-back of blood and the peripheral venous pressure increased thereby, surface varices and deep varices with congestion phenomena forming. The causes therefor may be a slowed circulation (e.g. in case of longer confinement to bed), constitutionally caused as a consequence of a congenital connective tissue weakness or as a consequence of other vein diseases. For local treatment, in most instances creams, ointments, gels and the like are used which contain heparin. Heparin has an antithrombotic effect due to its function as a catalyst, by inhibiting the serine proteases in the coagulation cascade. Thereby, a series of blood coagulation factors are inactivated. Yet in case of a tendency to bleeding and in case of thrombocytopenias, heparin must not be used. Furthermore, it should not get into contact with open wounds, the eyes or the mucous membranes. Besides, counter-reactions may occur easily on account of an hypersensitivity to heparin.

It is thus the object of the present invention to provide an agent for topical application which has a broad application spectrum and thus may be employed for a plurality of uses, which, however, also is composed of complex components which are as close to natural as possible, and thus is well tolerable without any negative side effects. A further object of the present invention consists in providing a completely new, natural and effective agent for treating hemorrhoidal diseases. A further object of the present invention consists in providing an agent against loss of hair. Still another object of the present invention is the provision of a topically usable agent for treating skin problems, such as e.g., wrinkle formation, acne, impure skin, sun burn, wounds etc., as well as an agent for fighting varicose veins.

According to the invention, these objects are achieved by the use of a substance mixture comprising honey and olive oil for preparing a medicament for topical application. With the use according to the invention, the per se known healing effects of honey and olive oil can be utilized, the therapeutical effects being increased in the topical application in synergistic manner.

By application on the skin to be treated, the ingredients can unfold their effect directly at the desired site and can quickly lead to a sure healing success. By the fact that the substance mixture according to the invention contains purely natural substances, the application is without contraindications and adverse side-effects, in contrast to synthetically produced medicaments which frequently contain chemically produced substances in unnaturally high concentrations and of which the use is not without risks.

In this instance, the treatment is based on the action of purely natural substances, whereby the risk of counter-reactions of any type, e.g. allergies, hypersensitivity to ingredients and the like, is greatly reduced. Furthermore, the hemorrhoidal disease is to be healed quickly by aid of the substance mixture according to the invention, and not merely alleviated, as is frequently the case with the present medicaments.

Although honey and olive oil alone or in the form of substance mixtures together with other substances are already known in the medical science, yet so far a mixture of honey and olive oil has never been used in topical treatment.

Because of its various and extensive healing and alleviating effects, honey has been used in the art of healing for many centuries.

There is a large variety of different types of honey which, depending on their ingredients, have different properties as regards their application in the medical field. The main component of honey is invert sugar, further sugars are cane sugar, maltose, and, depending on the plant species visited, more rarely occurring sugars originating from the latter. Besides, sugar, honey contains further enzymes, such as invertase, diastases, catalase, amylase, phosphatase, glucose oxidase, which, with the cooperation of the oxygen of air, convert dextrose into gluconic acid and hydrogen peroxide. The latter provides oxygen in an extremely reactive form which in turn is an excellent germ killer and preservative. One of the most important components of honey is pollen. Of the organic acids, malic acid, succinic acid, gluconic acid, acidic acid, formic acid, of the inorganic acids phosphoric acid and hydrochloric acid are present. Honey furthermore contains mineral substances in a portion of up to 3%, among them Fe, Cu, P, S, K, Na, Mg, Ca, Si, Mn, Cl, Zn and, in small amounts, also vitamins (B1, B2, B6, pantothenic acid, nicotinic acid, H, folic acid and little vitamin C) and, in very small amounts, nearly all the amino acids. Furthermore, hormones, acetyl choline, which is involved in the conduction of nerve impulses, inhibines (bactericides) and vegetable dyes, such as flavones or carotines, and aromatic substances (alcohols, aldehydes, ketones and essential oils) have been found ("Doktor Biene, Bienenprodukte—ihre Heilkraft und Anwendung" by Paul Uccusic, pp. 45–53, 2nd Edition, 1987, Wilhelm Heyne Verlag, Munich).

Honeydew honeys are rich in resins and essential oils and thus are considered for all diseases of the respiratory tract (bronchial catarrhs, but also as a supporting treatment of pulmonary tuberculosis and pneumonia), of the urogenital system (cystitis, urethriotis, prostatitis) and as a diuretic. Furthermore, a favorable effect can be found in case of gravel and renal calculi. Furthermore, a regulating effect has been postulated in case of problems of the portal circulation (hemorrhoids, congestion of the portal vein, inclination to venous thromboses). Honeys of mixed blossoms have a very favorable effect on allergic persons. Linden honey is sedating and antiseptic. Melissa honey is spasmolytic and sedating. Chestnut honey is generally blood-purifying, fights the tendency to thrombosis, thrombophlebitis and varicose veins, to mention but a few examples from the list of types of honey with the different healing properties ("Doktor Biene", pp. 64–71, supra). Also mixtures of honey and other vegetable substances are described which are applied for the most varying ailments: e.g., a paste made of equal parts of honey, olive oil and propolis against parodontosis and caries; a mixture of 95% rose honey, 5% borax for wounds, furuncles, exanthemas and eczemas; propolis dissolved in honey is a prevention against flu and running nose; honey and fennel syrup at the ratio of 1:1 helps in case of indigestion, flatulence, heat-burn and constipation. other known mixtures having a healing effect are honey with wine, honey with lavender or honey with edible chestnuts ("Doktor Biene", pp. 148–165, supra).

Also olive oil has already been used as a natural medicine against various ailments for a long time. Depending on its origin and recovery, olive oil contains from 95 to 99% acyl glyceroles, from 0.5 to 1.5% unsaponifyable substances and from 0.1 to 3% free fatty acids, glycerides, secciridoids and flavonoids. The composition of the fatty acid fraction obtainable upon saponification varies in dependence on the origin and degree of ripeness of the olives, oleic acid, palmitic acid and linoleic acid being the main components. Furthermore, phenolic compounds, carbohydrates (mainly squalene), steroles, triterpene alcohols, hydroxy triterpenic acids, tocopheroles, phospholipids, carotinoids, chlorophyll and pheophytines occur ("Hagars Handbuch der pharmazeutischen Praxis" by R. Hänsel, K. Keller, H. Rimpler, G. Schneider (Editors), Vol. 5, Drogen E–O, pp. 940–945, 5th Edition, 1993, Springer Verlag).

According to the prior art, olive oil is, e.g., used in case of cholangitis, cholelithiasis, ikterus, flatulence, meteorism, dysbacteria, Roemheld Syndrome, obstipation and as an intestinal lubricant. Moreover, olive oil has been administered in case of diseases of the biliary tract, for treating ulcers of the stomach and of the intestines, in case of renal calculi, as well as in the form of an emulsion as a diet rich in nitrogen in case of renal failure. Also for wound care in case of slight burns and in case of psoriasis, for softening the crusts in case of eczemas and as a massage lubricating oil in aqueous emulsion in case of sun burn, as a massage oil for the treatment of rheumatism as well as in case of hemorrhages, olive oil has been used ("Hagars Handbuch der pharmazeutischen Praxis", supra).

Although, as mentioned above, honey and olive oil have been used for a whole series of healing purposes, it has been shown within the scope of the present invention that by a combination of honey and olive oil in a suitable ratio, these substances have a particularly healing effect which—if applied topically—quickly occurs directly at the site to be treated, and lead to certain success when diseases occurring on or directly under the skin are treated. It has been shown that use of the substance mixture will be particularly suitable if an agent is used which contains from 50–90% of honey. If honey constitutes the major portion of the substance mixture (at least more than one half), its regulating effect is particularly enhanced by the addition of olive oil, primarily in case of problems of portal circulation (hemorrhoids, congestion of the portal vein, inclination to venous thromboses) and in case of an inclination to thromboses, thrombophlebitis and varicose veins. If honey constitutes approximately 60% of the substance mixture, the maximum healing effect against these ailments seems to be reached. A mixture of honey from blossoms, wild honey, acacia (robinia) honey is suitable.

A particularly advantageous effect of the substance mixture according to the invention is attained if the mixture contains 5 to 20% of olive oil. An addition of approximately 8.5% of olive oil is optimal.

In the use according to the invention, it is advantageous to provide a substance mixture comprising additionally one, several or all of the following substances: beeswax, propolis, camomile, sage, Aloe vera, thyme, lavender and/or diverse oils, such as St. John's-wort, wheatgerm oil and others.

Beeswax is used in the cosmetic and medical branches for preparing cremes and ointments, where it acts emulsifying. Like honey, propolis and royal jelly, beeswax has therapeutical properties and thus is substantially better suited for preparing cremes than wax of mineral origin ("Aromatherapie von A–Z" by Patricia Davis, p. 77, 1998, Knaur-Verlag). From the chemical point of view, waxes consist of fatty acids which are esterified with higher alcohols, propolis, colorants and vitamin A. Wax has always been used as a wound pad and against skin diseases, for enbalming corpses and in odour (aroma) therapy. In cosmetics, wax is used as a component of facial packs or depilatory agents ("Doktor Biene", pp. 136–139, supra).

Propolis has no constant chemical composition. Depending on its region of origin, this substance consists of approximately 55% resinous and balm substances, approximately 30% wax, 5 to 10% essential oils, approximately 2 to 5% pollen, vitamins and microelements ("Propolis—Heilkraft aus dem Bienenvolk" by Klaus Nowottnick, pp. 26–31, Leopold Stocker Verlag, 1994). Propolis has comprehensive and highly effective inhibiting and killing actions on numerous bacterial strains, fungicidal properties and has a distinctly virucidal activity. Moreover, highly anesthesising properties could be demonstrated, it is active against indigestion, skin diseases and contusions and has tissue protective and wound-healing properties. In various apitherapy clinics, an overwhelming success has been achieved in case of coronary and circulatory diseases by using a combination of royal jelly with propolis, pollen and pumpkin seeds. Propolis could also cure various diseases of the throat, nose and ear as well as bronchial and lung diseases ("Naturheilung mit Honig—Gesundheit aus der Natur" by Arne Lund, pp. 34–71, Ludwig Verlag). Many physicians treat varicose veins and peripheral circulatory disturbances, periproctic abcesses, hemorrhoids and anal fistulas with propolis ("Doktor Biene", pp. 110–133, supra). These properties can optimally be utilized for the substance mixture of the invention, whereby the healing effect, in particular in respect of circulatory disturbances, is increased.

Camomile (Chamaemelum, Chamomilla) as a medicinal additive is widely used in the medical field and is also extremely advantageous for the substance mixture according to the invention. The ingredients of camomile substantially are essential oils, sesquiterpenes, hydroperoxides, polyphenols, polyines, triterpenes and steroids. The activity of camomile is extensive: antiphlogistic, musculotropically spasmolytic, wound healing promoting, deodorising, antiseptic and disinfectant, promoting the skin metabolism, to mention but a few properties ("Hagars Handbuch der pharmazeutischen Industrie", by R. Hänsel, K. Keller, H. Rimpler, G. Schneider, Vol. 4, Drogen A–D, pp. 807–830, 5th Edition, 1992, Springer Verlag). By adding camomile to the substance mixture according to the invention, the former acts further pain alleviating, cramp-alleviating, anti-inflammatory, and furthermore, the treatment of hemorrhoids is improved.

Sage (Salvia) contains essential oils, hydroxy cinnamic acids, depsides, flavonoids, di- and triterpenes and trace elements. Sage i.a. has antimicrobial, antiviral, antihydrotic, spasmolytic, anti-irritant, antihypertensive, choleretic, central and antidiabetic activities ("Hagars Handbuch der pharmazeutischen Praxis" by R. Hänsel, K. Keller, H. Rimpler, G. Schneider, Vol. 6, Drogen P–Z, pp. 538–567, 5th Edition, 1994, Springer Verlag). Due to these manifold properties, in a preferred embodiment, sage is admixed to the substance mixture, whereby it has an increased anti-inflammatory and wound-healing effect.

Aloe vera is the thickened juice of the leaves of Aloe barbadensis, and besides resins, anthranoids, emodin, essential oils and the like, it contains 15–40% aloin, a bitter tasting, yellowish anthron derivative, which is very popular among people as a laxative. Its effect is due to an irritation of the intestinal mucosa and starts already after a few hours. Other ailments are treated by aid of Aloe Vera: inflammations of the anus, arteriosklerosis, purulent wounds and injuries, traumatic erysipelas, duodenal ulcer, migrating cheilitis, loss of hair, hemorrhoids, varicose veins, dermatomycoses, for skin care and blood purification ("Aloe Vera—Die Königin der Heilpflanzen" by Alice Beringer, pp. 13–53, Hyene Bücher, 1997, Wilhelm Hyene Verlag, München). In the substance mixture according to the invention, Aloe vera promotes the moisturizing and blood-flow stimulating effects, which has an extremely positive effect on the diseases to be treated.

The ingredients of thyme (Thymus vulgaris) are essential oils, tannins, phenol carboxylic acids, carbohydrates, triterpenes, aluminum and various biphenyl derivatives. Thyme has antimicrobial, antiviral, insecticidal, spasmolytic, wound healing, anthelmintic and antioxidative effects, furthermore thyme inhibits the prostaglandin synthesis and influences the metabolism of medicaments ("Hagars Handbuch der pharmazeutischen Praxis" by R. Hänsel, K. Keller, H. Rimpler, G. Schneider, Vol. 6, Drogen P–Z, pp. 974–989, 5th Edition, 1994, Springer Verlag). Therefore, preferably also thyme is admixed to the substance mixture according to the invention, whereby the wound-healing and anti-inflammatory action as well as the antipruritic action are enhanced and improved.

A further possible and desirable additive to the substance mixture according to the invention is lavender (Lavandula). The ingredients of lavender i.a. are essential oils, tannins, phenyl carboxylic acids. Among the most important actions are chloretic and cholagogic, hypoglycemic, scar-smoothing, pain-alleviating and spasmolytic, antimicrobial and expectoral action ("Hagars Handbuch der pharmazeutischen Praxis" by R. Hänsel, K. Keller, H. Rimpler, G. Schneider, Vol. 5, Drogen E–O, pp. 621, 630, 634, 642, 5th Edition, 1993). By the addition of lavender, the substance mixture of the invention is particularly active against hardening of the muscles, wounds which do not heal well, chronic eczemas in the intestinal and anal region as well as for stimulating circulation.

Further oils, such as St. John's wort, almond oil, rose oil or wheatgerm oil, e.g., round off the ingredients of the preparation.

A particularly favorable effect of the substance mixture is attained if it comprises 10–30%, preferably 18% of beeswax, 1–15%, preferably 5% of propolis, and/or 1–10%, preferably 2% of camomile, and/or 1–10%, preferably 2% of sage, and/or 1–10%, preferably 5.3% of Aloe vera, and/or 0.1–10%, preferably 1% of thyme, and/or 0.01–5%, preferably 0.2% of lavender. By this, the properties of the different substances are optimally utilized because they are harmonized. In doing so, one, several or all of them may be admixed, yet particularly suitable is a substance mixture in which. all of them are contained in the portion characterized by "preferably".

An advantageous variant of the substance mixture consists in that it comprises further vegetable substances, such as, e.g., birch oil, Bois Bondee bark, royal jelly, jasmine, St. John's wort oil, marjoram, myrrh, almond oil, peppermint, pollen, rose oil, rosemary, sandalwood, milfoil, wheatgerm oil, cedar oil, cinnamon and/or cypress.

The substance mixture, however, is not restricted to the above-mentioned ingredients, but additional components may be added, thus, e.g., further essential oils, vitamins, fatty acids, mineral substances, carbohydrates, organic and inorganic acids and other substances which advantageously may be admixed if the specific application calls for it.

One suitable embodiment of the substance mixture of the invention is present if the mixture additionally contains homeopathic substances. These homeopathic substances may either increase the healing effect of the inventive substance mixture by their particular properties, or they may cause additional effects, depending on the homeopathic substance admixed.

A particularly advantageous use of the substance mixture of the invention consists in preparing a remedy for treating hemorrhoidal diseases. As has been mentioned, the known effect of honey against hemorrhoids can be increased and enhanced according to the invention by the presence of olive oil such that hemorrhoidal diseases not only are alleviated but can effectively be removed (cf. Example 1). In contrast to the medicaments described in the prior art, the substance mixture according to the invention acts rapidly and reliably removes hemorrhoids, as is also demonstrated in the Examples. A substance mixture independently comprising 30–80%, in particular 50–60% of honey, 1–20%, in particular 7–10% of olive oil, and 1–30%, in particular 15–20% of beeswax, is preferably used.

A further advantageous use of the substance mixture according to the invention consists in preparing an agent for hair and skin care, preferably against the loss of hair, dandruff formation and dehydration. These properties, too, (anti-inflammatory, antibacterial, and antimycotic effects; stopping of itching, burning, skin irritations, and of eczema formation and thus the stopping of the main causes of dandruff formation; improving circulation and activation of the function of the diseased root; supply with vitamins, trace elements, natural glucose, amines; enbalming of scalp and hair, whereby a dehydration is prevented) have been demonstrated in several tests (cf. Example 2). These effects have not even been described for the individual components of the substance mixture in the prior art. Preferably, a substance mixture independently comprising 10–40%, in particular 20–30%, of honey, 1–10%, in particular 4–6%, of olive oil, and 1–40%, in particular 15–25%, of Aloe vera.

Another advantageous use of the substance mixture according to the invention consists in the preparation of an agent for skin care (cf. Example 3). This agent is particularly effective in the treatment of wrinkles formed, acne, impure skin, sun burn, wounds, environmental damage as well as (purulent) inflammations of the skin of the most varying causes. The substance mixture of the invention not only is applied if problems already exist, it may also be applied prophylactically to protect against environmental influences. Preferably, a substance mixture independently comprising 10–40%, in particular 15–25%, of honey, 1–30%, in particular 10–20%, of olive oil, and 10–50%, in particular 20–40%, of Aloe vera is used.

A further advantageous use of the substance mixture according to the invention consists in the preparation of an agent against varicose veins. Here, honey and olive oil, if applied topically, act to activate circulation.

The agent to be used according to the invention may be prepared in all the application forms common for topical medicaments, in particular as an ointment, emulsion, sponge, soap, shampoo, facial pack, bath salts, plaster, stocking, lotion, . . .

According to a further aspect, the present invention relates to a substance mixture comprising 50–90% of honey, and olive oil. Optimally, the substance mixture comprises approximately 60% of honey. It has been shown that the positive properties of the ointment are best utilized if the honey is a mixture of honey from blossoms, wild honey and acacia (robinia) honey.

Advantageously, the substance mixture according to the invention comprises 5–15% of olive oil. Optimal is an addition of approximately 8.5% of olive oil, since the agent according to the invention then is most effective against hemorrhoidal ailments.

Furthermore, it is suitable if the substance mixture additionally comprises one, several or all of the following substances: beeswax, propolis, camomile, sage, Aloe vera, thyme and/or lavender.

A particularly advantageous substance mixture is obtained if it comprises 10–30%, preferably 18%, of beeswax, 1–15%, preferably 5%, of propolis, and/or 110%, preferably 2%, of camomile, and/or 1–10%, preferably 2%, of sage, and/or 1–10%, preferably 2%, of Aloe vera, and/or 0.1–10%, preferably 1%, of thyme, and/or 0.01–5%, preferably 0.2%, of lavender.

Furthermore, it is advantageous if the substance mixture comprises additional components, such as further vegetable substances (such as, e.g., birch oil, Bois Bondee bark, royal jelly, jasmine, St. John's wort oil, marjoram, myrrh, almond oil, peppermint, pollen, rose oil, rosemary, sandalwood, milfoil, wheatgerm oil, cedar wood oil, cinnamon and/or cypress), homeopathic substances or mixtures of these components. Furthermore, the substance mixture of the invention may also comprise substances which assist in its application or storage stability, such as, e.g., stabilizers, preservatives, pharmaceutical adjuvants, buffer substances, thickening agents, emulsifiers, . . .

The invention will be further explained by way of the following Examples, to which, of course, it is not restricted.

EXAMPLE 1

Treatment of Patients Afflicted with Hemorrhoids

Composition of Ointment:

Honey (55%), wherein 30% of honey from blossoms, 30% of acacia (robinia) honey and 40% of wild honey are contained, olive oil (8.5%), propolis (5% of a 40% tincture), beeswax (18%), camomile tincture, sage tincture, lavender, thyme, Aloe vera, wheatgerm oil.

36 patients afflicted with hemorrhoids (21 women aged between 23 and 64 years, and 15 men aged between 25 and 66 years) were treated for 4 weeks with the following application prescription, the ointment being applied 3 times per day during the first week and twice per day in the following weeks: The elongated portion of the tube of the ointment was introduced into the rectum by about 3–5 cm, the ointment was injected according to the patient's feeling while the elongated portion of the tube was slowly retracted. The ointment was also applied around the anus, then allowed to dry, and any desired sanitary napkin was used (without wiping off). After approximately 20 min, the sanitary napkin was removed.

Shortly after the application, slight burning was experienced in some cases, yet subsequently the good feeling of the easing of the pain and of the antipruritic effect set in until the discomfort had disappeared.

With the plurality of test subjects, the hemorrhages stopped on the second day, with the complaints largely gone. In 8 patients, the hemorrhages stopped on the sixth day and a substantial improvement set in; these patients, however, had suffered from hemorrhoids already for between 2 and 11 years.

16 of the test persons were additionally afflicted with perianal thromboses; also for this disease an extensive regression was experienced under treatment. For 3 patients, surgery had been planned because of their hemorrhoidal disease, the indication of which had been diagnosed by a specialist. After the treatment this indication was no longer present (also determined by the specialist).

EXAMPLE 2

Treatment of Patients Suffering from Loss of Hair

Composition of hair pack: honey (25%), wherein 40% acacia (robinia) honey, 30% wild honey and 30% honey from blossoms are contained, olive oil (4.9%), propolis (3% of a 40% tincture), Aloe vera (20%), camomile tincture, lavender oil, marjoram oil, milfoil tincture, ceder oil, sandalwood tincture, birch oil, myrrh tincture, rosemary oil, pure royal jelly, pure pollen, rose oil as well as biobase mass and alcohol.

The preparation was tested as follows, 2–3 times per week, for about 3 months, on 7 test persons who suffered from loss of hair: After having washed the hair with a mild shampoo, the hair pack was applied to the towel-dried hair and to the scalp. After a reaction time of 20–30 min, the pack was thoroughly rinsed out with luke-warm water, and subsequently the hair was gently dried.

With 5 persons, the loss of hair stopped. One test subject (duration of illness: 3 months) showed renewed hair growth in areas with already sparse hair growth. With the test person with the longest duration of illness (15 months), the preparation had no effect.

EXAMPLE 3

Preparation of a Skin-Care Facial Pack

The following components are mixed to a facial pack according to the invention: honey (20%), olive oil (15%), propolis (8%), Aloe vera (30%), sage tincture, myrrh tincture, camomile tincture, basic substance for a biological creme.

This facial pack can be applied as a creme and be used like a conventional facial pack. The preparation according to the invention is applicable both by day and by night, after a preceding gentle cleaning of the skin.

What is claimed is:

1. A method for treating hemorrhoidal diseases in a patient, comprising topically administering to the patient a preparation comprising effective amount of honey, olive oil, propolis, aloe Vera, and sage.

2. The method of claim 1, wherein said preparation comprises 50% to 90% honey.

3. The method of claim 1, wherein said preparation comprises 5% to 10% olive oil.

4. The method of claim 1, wherein said preparation comprises 1% to 15% propolis.

5. The method of claim 1, wherein said preparation comprises 1% to 10% sage.

6. The method of claim 1, wherein said preparation comprises 1% to 10% aloe vera.

7. The method of claim 1, wherein said preparation comprises 50% to 90% honey, 5% to 10% olive oil, 1% to 15% propolis, 1% to 10% aloe vera, and 1% to 10% sage.

8. The method of claim 1, wherein said preparation further comprises at least one substance selected from the group consisting of beeswax, chamomile, thyme, lavender and diverse oils.

9. The method of claim 1, wherein said preparation comprises, independently of each other, 30% to 80% honey, 1% to 20% olive oil, and further comprising 1% to 30% beeswax.

10. The method of claim 1, wherein said preparation comprises, independently of each other, 50% to 60% honey, 7% to 10% olive oil, and further comprising 15% to 20% beeswax.

11. The method of claim 8, wherein said preparation comprises 10% to 30% beeswax.

\* \* \* \* \*

UNITED STATES PATENT AND TRADEMARK OFFICE
CERTIFICATE OF CORRECTION

PATENT NO.   : 6,482,442 B1
DATED        : November 19, 2002
INVENTOR(S)  : Suleiman Dado It is certified that error appears in the above-identified patent and that said Letters Patent is hereby corrected as shown below:

<u>Column 9,</u>
Line 9, please insert -- or preventing -- following "treating".
Line 11, please delete "amount" and insert -- amounts -- therefor.
Line 12, please delete "Vera" and insert -- vera -- therefor.

Signed and Sealed this

Fourth Day of March, 2003

JAMES E. ROGAN
*Director of the United States Patent and Trademark Office*